United States Patent [19]
Kodama et al.

[11] Patent Number: 5,654,289
[45] Date of Patent: Aug. 5, 1997

[54] DISACCHARIDE DERIVATIVE

[75] Inventors: Tohru Kodama; Masayuki Saitoh; Tomohiko Ogawa, all of Osaka, Japan

[73] Assignee: Suntory Limited, Osaka, Japan

[21] Appl. No.: 433,354

[22] PCT Filed: Mar. 9, 1994

[86] PCT No.: PCT/JP94/00376

§ 371 Date: May 5, 1995

§ 102(e) Date: May 5, 1995

[87] PCT Pub. No.: WO95/07285

PCT Pub. Date: Mar. 16, 1995

[30] Foreign Application Priority Data

Sep. 7, 1993  [JP]  Japan .................................. 5-222449

[51] Int. Cl.$^6$ .................... A61K 31/73; C07H 5/06; C07H 11/04; C07H 13/12
[52] U.S. Cl. .................. 514/53; 514/62; 536/53; 536/55.2; 536/123.13; 536/117; 536/121
[58] Field of Search ............... 536/53, 55.2, 123.13, 536/117, 121; 514/53, 62

[56] References Cited

FOREIGN PATENT DOCUMENTS 59-48497   3/1984   Japan .
61-227586  10/1986  Japan .

OTHER PUBLICATIONS

FEBS, vol. 332, No. 1.2, issued Oct. 1993, Ogawa, "Chemical Structure of Lipid a from *Porphyromonas (Bacteroides) gingivalis* Lipopolysaccharide", pp. 197–201.

Importance of Fatty Acid Substituents of Chemically Synthesized Lipid A–Subunit Analogs in the Expression of Immunopharmacological Activity, Infection and Immunity, Jan. 1988, vol. 56, No. 1, pp. 149–155.

Highly Purified Lipid X is Devoid of Immunostimulatory Activity, The Journal of Biological Chemistry, vol. 265, No. 16, pp. 9159–9164 (1990).

Structure of the Lipopolysaccharide from an *E. coli* Heptose–less Mutant, Marcha et al., The Journal of Biological Chemistry, vol. 254, No. 13, 5906–5917 (1979).

Ogawa et al., "Ripido A Ruijitai no Seibutsu Kassei (Biological Activiities of Lipid A Analogs)", Taisha (Metabolism), vol. 26, No. 5, pp. 15–27 (1989).

Honma Yudotai "(Synthetic Lipid A and its Derivatives)", Meneki Yakuri (Immunopharmacology), vol. 8, No. 4, pp. 25–32 (1990).

*Primary Examiner*—John Kight
*Assistant Examiner*—Everett White
*Attorney, Agent, or Firm*—Cushman Darby & Cushman IP Group of Pillsbury Madison & Sutro LLP

[57] ABSTRACT

A novel disaccharide derivative represented by the following formula, which is the compound of the present invention, its stereoisomers and salts and a medicinal composition comprising the same as an active ingredient.

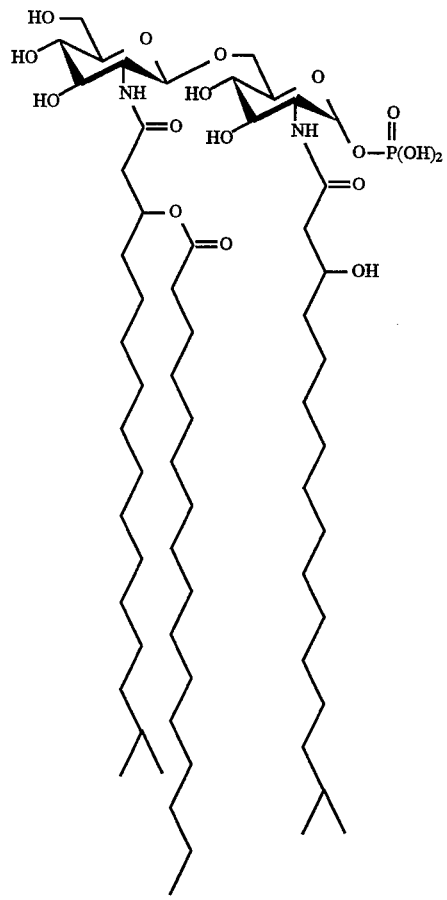

The compound of the present invention has various biological activities, for example, potent mitogenic activity, adjuvant activity, polyclonal B cell activating (nonspecific protective) activity, natural killer activity, antitumor activity, antiviral activity, etc. but little harmful effects, for example, function of inducing the production of so-called inflammatory cytokines such as tumor necrosis factor (TNF) and IL-1 from macrophages. Therefore it is highly useful as an immunopotentiator, an antitumor agent, an antiviral agent as well as an agent for preventing and treating sepsis, chronic rheumatoid arthritis, etc. without showing any harmful effects such as lethal toxicity or pyrogenicity as observed in the conventional lipid A and derivatives thereof.

2 Claims, No Drawings

DISACCHARIDE DERIVATIVE

DESCRIPTION

1. Technical Field

This invention relates to a novel disaccharide derivative, which has various biological activities and a low toxicity (i.e., extremely low lethal toxicity and pyrogenicity), and its salt.

2. Background Art

Lipopolysaccharide (LPS), which is contained in the outer membrane of the cell wall of various gram-negative bacteria, consists of a glycolipid called "lipid A" to which various saccharides are bonded. It has been known for a long time that LPS is the main component of endotoxins. It is also known that LPS accelerates various immune functions in vivo and its main activity expression site resides in lipid A. It is understood that LPS has various biological activities in addition to an immunomodulatory effect and an antitumor effect.

The chemical structure of lipid A has been clarified in various gram-negative bacteria including *Escherichia coli* ["Structure of the lipopolysaccharide from an *E. coli* Haprose-less Mutant", Marcha R. R., Jiunn-yann T., Israel B., and H. Gobind Khorana, The Journal of Biological Chemistry, vol. 254, No. 13, pp. 5906–5917 (1979)]. Among all, the chemical synthesis of lipid A originating in *Escherichia coli* has been completed and various derivatives thereof are also chemically synthesized. As a result, it is proven that some of chemically synthesized lipid A derivatives are comparable or even superior to the lipid A originating in *Escherichia coli* in the function of inducing tumor necrosis factor (TNF) and mitogen activity [Japanese Patent Application Laid-Open (Kokai) No. Sho-59-48497].

However, the lipid A originating in *Escherichia coli* and its derivatives exhibit some unfavorable properties such as pyrogenicity and necrotoxic activity. Thus attempts were made to synthesize lipid A derivatives over an extended range [Japanese Patent Application Laid-Open (Kokai) No. Sho-61-227586]. Further, detailed studies were conducted on compounds having a monosaccharide structure with lipid A-like activities, modification with the use of various substituents and substituent-introduction sites. Also various analogs were synthesized and the biological activities, immunological activities and toxicities of these substances were examined ["Ripido A Ruijitai no Seibutsu Kassei (Biological Activities of Lipid A Analogs)", Ogawa H., Kiso M. and Hasegawa A., Taisha (Metabolism), vol. 26, No. 5, pp. 15–27 (1989); and "Gosei Ripido A to sono Yudotai (Synthetic Lipid A and its Derivatives)", Honma Y., Meneki Yakuri (Immunopharmacology), vol. 8, No. 4, pp. 25–32 (1990)]. However, no reference has been made concerning a compound having free hydroxyl groups at the 3, 3' and 4'-positions and no compound practically available as a medicine has been developed so far.

DISCLOSURE OF THE INVENTION

Under these circumstances, it has been strongly desired to develop a lipid A analog which has a reduced toxicity and enhanced activities.

The present invention provides a novel disaccharide derivative which has various useful biological activities, for example, potent mitogen activity, adjuvant activity, nonspecific protective activity, antiviral activity, immunopotentiation function, etc. but little adverse effects, for example, pyrogenicity, lethal toxicity, etc. and is highly useful as a medicine, etc.

The present inventors have found that LPS contained in the outer membrane of cell wall of *Porphyromonas* (*Bacteroides*) *gingivalis*, which is one of bacteria commonly found in human oral cavity and seemingly being causative of periodontal diseases, has mitogen activity, etc. but yet extremely low lethal toxicity and pyrogenicity. They have further prepared and purified the activity expression site of this LPS, analyzed its structure and effected extensive studies thereon. As a result, they have found that the active compound of the present invention has a glucosamine $\beta(1,6)$-disaccharide structure having a phosphate group bonded to the 1-position as the basic skeleton and 3-hydroxy-15-methylhexadecanoic acid is bonded to the amino group at the 2-position thereof via an amide linkage while 3-hexadecanoyloxy-15-methylhexadecanoic acid is bonded to the amino group at the 2'-position thereof via an amide linkage. Thus the structure of the compound of the present invention is characterized in that it has no phosphate group at the 4'-position and the hydroxyl groups at the 3- and 3'-positions remain in a free state, largely differing from the conventional lipid A derivatives. It is therefore assumed that the compound of the present invention has a structure represented by the following Formula I.

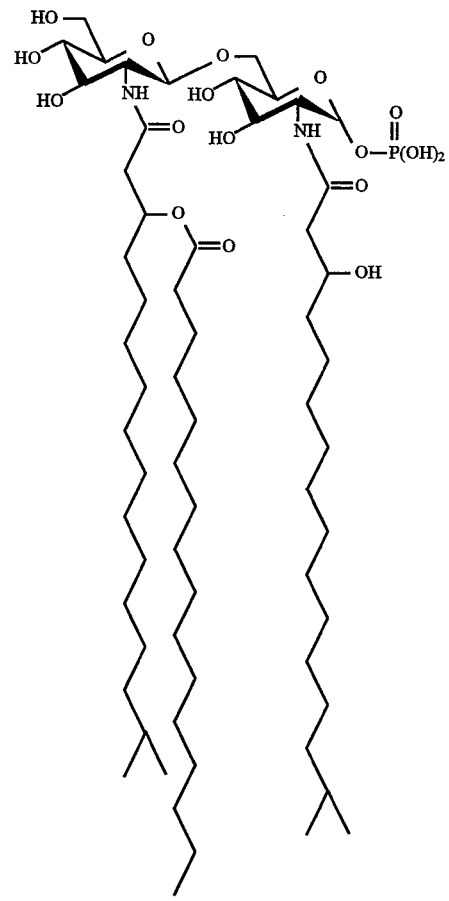

It has been further found that the compound of the present invention has various biological activities, for example, potent mitogen activity, adjuvant activity, polyclonal B cell activation (nonspecific protective) activity and natural killer activity, but yet little activity of inducing the production of so-called inflammatory cytokines such as tumor necrosis factor (TNF) and IL-1 from macrophages as observed in the conventional lipid A and its derivatives. Accordingly, the compound of the present invention is useful as an immunopotentiator being free from any adverse effects such as lethal toxicity or pyrogenicity which arise in the case of the conventional lipid A and its derivatives.

It has been further found that the compound of the present invention suppresses the production of IL-1, which is induced by lipid A of *Escherichia coli*, and induces the production of IL-1 receptor antagonist (IL-1ra). Together with the potent nonspecific protective activity as described above, these activities make the compound useful as an agent for preventing and treating pathologic conditions induced by the infection with gram-negative bacteria such as *Escherichia coli*, in particular, sepsis or septic shock. Because of being capable of suppressing the production of IL-1 and inducing the production of the IL-1 receptor antagonist (IL-1ra), furthermore, the compound of the present invention is useful as a remedy for pathologic conditions accompanied by the abnormal production of IL-1 per se, for example, chronic rheumatoid arthritis, etc.

It has been also found that this compound activates natural killer cells and shows an antitumor activity and an antiviral activity. The antitumor activity suggests that it is useful as an antitumor agent, while the antiviral activity and the potent nonspecific protective activity indicate its usefulness as an antiviral agent.

Based on these characteristics, it is expected that the novel disaccharide derivative according to the present invention or its salt is particularly useful in a medicinal composition which comprises this compound together with pharmaceutical carriers and/or diluents.

Although the compound of the present invention may exist in the form of various stereoisomers, individually isolated isomers and isomeric mixtures are all involved in the technical idea of the present invention. The compound of the present invention can be prepared and purified from a microbial source and then used. Alternatively, it can be produced by various chemical synthesis techniques.

Now specific examples of the production of the compound of the present invention by each method will be given.

(1) Production example with the use of microorganism

In order to produce the compound of the present invention from a microorganism, any microorganism can be used so long as it can produce the compound of the present invention represented by the above Formula I. For example, *Porphyromonas* (*Bacteroides*) *gingivalis* (ATCC Catalogue No. 33277) is usable therefor.

Although either a liquid medium or a solid one may be used in the incubation, it is usually convenient to effect anaerobic stationary culture in a liquid medium. Any medium may be employed, so long as the microorganism producing the compound of the present invention can grow and produce the compound of the present invention therein. The conditions for incubation (temperature, period, properties of medium, etc.) may be appropriately selected and controlled in such a manner as to give the maximum yield of the compound of the present invention. It is preferable that the incubation is effected under anaerobic conditions at a temperature of 25° to 40° C., still preferably at 37° C., for 12 to 36 hours, still preferably for 26 hours and the pH value of the medium is maintained at 6.0 to 8.0, still preferably at 7.3.

The compound of the present invention is produced and accumulated by incubating the microorganism under the above-described conditions. Then the cells are collected from the culture medium by filtration or centrifugation and the target compound is separated and purified therefrom. To separate and purify LPS from the cells, various means may be selected depending on the chemical properties of the compound. For example, LPS can be separated and purified by appropriately combining separation and purification techniques, for example, extraction with hot phenol-water, treatment with various enzymes, centrifugation, solvent fractionation and column chromatography with the use of various resins. After repeatedly purifying, the LPS or crude LPS thus obtained is hydrolyzed with a weak acid. This hydrolysis may be carried out by any method, so long as the compound of the present invention is thus liberated. Preferably, the hydrolysis is effected with the use of 0.05 to 0.2N acetic acid at a temperature of 90° to 110° C. for 2 to 3 hours. The target compound may be separated and purified from the reaction mixture by various techniques selected depending on the chemical properties of the compound of the present invention. Namely, solvent fractionation and column chromatography with the use of various resins may be employed. By appropriately combining these techniques, the compound of the present invention can be separated and purified.

(2) Production example via chemical synthesis

An N-glucosamine derivative, which has been protected with an appropriate protecting group at an appropriate position, is converted into a disaccharide derivative via a glycosidation reaction. Then the disaccharide derivative is N-acylated with a fatty acid and phosphorylated at the 1-position at the reducing end followed by deblocking. Alternatively, a protected N-glucosamine derivative, which has been N-acylated with a desired fatty acid, is converted into a disaccharide derivative via a glycosidation reaction. Then the disaccharide derivative is phosphorylated and deblocked.

The compound of the present invention thus obtained is a compound capable of forming a salt at its phosphate moiety. Therefore it can be easily converted into a salt by a publicly known method. Examples of such salts include alkali metal salts for example, sodium salt, potassium salt, etc.; alkaline earth metal salts for example, calcium salt, magnesium salt, etc.; ammonium salts and pharmaceutically acceptable amine salts. Examples of nontoxic amine salts include tetraalkylammonium salts for example, tetramethylammonium salt, etc.; and organic amine salts for example, methylamine salt, triethylamine salt, cyclopentylamine salt, benzylamine salt, pyridine salt, piperidine salt, diethanolamine salt, lysine salt, arginine salt, etc.

The disaccharide derivative, i.e. the compound of the present invention, or its salt thus obtained may be administered in the form of a medicinal composition for therapeutic or preventive purposes either systemically or topically and either orally or parenterally. Although the administration dose varies depending on age, body weight, conditions, administration route, etc., it is usually administered to an adult in a single dose of from 0.01 to 100 mg once to several times per day either orally or parenterally. As a matter of course, the dose varies depending on various factors. Thus a satisfactory effect can be achieved in some cases by administering the compound in a smaller dose than the lower limit as specified above, while it is sometimes needed to administer the compound in a dose exceeding the upper limit as specified above.

A Solid medicinal composition of the present invention for oral administration includes tablets, powders, granules, etc. In such a solid composition, the compound of the present invention is mixed with at least one inert diluent, for example, lactose, glucose, microcrystalline cellulose, starch, polyvinyl pyrrolidone, magnesium metasilicate aluminate, etc. In addition to the inert diluent, the composition may contain other additives such as a lubricant for example, magnesium stearate or a disintegrating agent for example, cellulose calcium gluconate. Tablets or pills may be coated with a gastric or enteric coating film made of, for example, sucrose, gelatin, hydroxypropylcellulose, etc., if necessary. Also, they may be coated with two or more layers. It is also possible to use capsules made of a material such as gelatin which can be taken up by human body.

A liquid medicinal composition for oral administration includes pharmaceutically acceptable emulsions, solutions, suspensions and syrups. Examples of inert diluents generally employed in the art therefor include purified water, ethanol, etc. In addition to the inert diluent, the liquid composition may contain auxiliaries such as a humectant, a suspending agent, etc. and additives such as a sweetening agent, a flavor, an antiseptic, etc. The composition for oral administration also includes sprays which are formulated in a conventional manner. An injection composition of the present invention for parenteral administration includes sterile aqueous or nonaqueous solutions, suspensions and emulsions. Aqueous solutions and suspensions contain, for example, distilled water for injection and physiological saline. Nonaqueous solutions and suspensions contain, for example, propylene glycol, polyethylene glycol, vegetable oils such as olive oil, alcohols such as ethanol, Polysorbate 80 (registered trademark), etc. Such a composition may further contain auxiliaries such as an antiseptic, a humectant, an emulsifier or a dispersion aid. These compositions are sterilized by a specific filtration technique, addition of a bactericide or irradiation. It is also possible to prepare a sterile solid composition which is dissolved in sterile water or a sterile solvent for injection before use. Compositions for parenteral administration also involve liquid preparations for external use, embrocations such as ointments, suppositories, pessaries, etc. each formulated by a publicly known method.

It has been found that the compound of the present invention has various biological activities, for example, potent mitogenic activity, adjuvant activity, polyclonal B cell activation (nonspecific protective) activity, natural killer activity, etc., but little activity of inducing the production of so-called inflammatory cytokines such as tumor necrosis factor (TNF) and IL-1 from macrophages as observed in the conventional lipid A and its derivatives. Accordingly, the compound of the present invention is free from any adverse effects such as lethal toxicity or pyrogenicity, which cause troubles in the conventional lipid A and its derivatives, and thus useful as an immunopotentiator.

It has been further found that the compound of the present invention suppresses the production of IL-1 induced by lipid A of Escherichia coli and induces the production of IL-1 receptor antagonist (IL-1ra). Together with the potent non-specific protective activity, these activities make the compound of the present invention useful as an agent for preventing and treating pathologic conditions induced by the infection with gram-negative bacteria such as Escherichia coli, in particular, sepsis or septic shock. Due to its ability to suppress the production of IL-1 and inducing the production of the IL-1 receptor antagonist (IL-1ra), furthermore, the compound of the present invention is useful as a remedy for pathologic conditions accompanied by the abnormal production of IL-1 per se, for example, chronic rheumatoid arthritis, etc.

It has been also found that this compound activates natural killer cells and shows an antitumor activity and an antiviral activity. The antitumor activity suggests that it is useful as an antitumor agent, while the antiviral activity and the potent nonspecific protective activity indicate its usefulness as an antiviral agent.

Based on these characteristics, it is expected that the novel disaccharide derivative according to the present invention or its salt is particularly useful in a medicinal composition which comprises this compound together with pharmaceutical carriers and/or diluents.

Now the compound according to the present invention will be described in greater detail. However, it is to be understood that the present invention is not restricted to the specific embodiments described therein.

EXAMPLE 1: Production from microorganism

Porphyromonas (Bacteroides) gingivalis was anaerobically incubated in 160 l of a GAM bouillon (manufactured by Nissui Seiyaku K.K.) medium (pH 7.3) at 37° C. for 26 hours. After the completion of the incubation, the cells were collected by centrifuging the culture medium and freeze-dried. Thus 100 g of dry cells were obtained. These dry cells were extracted by the hot phenol-water extraction method to thereby give crude LPS. Namely, 3.5 l of distilled water was added to 100 g of the dry cells and heated to 68° C. Separately, 90% phenol was heated to 68° C. and added thereto. The resulting mixture was then stirred at 68° C. for 20 minutes, cooled with ice and centrifuged. The aqueous layer was collected and 3.5 l of distilled water was added again. After repeating the extraction procedure, the aqueous layers thus obtained were combined, sufficiently dialyzed against distilled water, concentrated and freeze-dried. Thus 12.47 g of a crude extract was obtained. Ten g of this crude extract was suspended in 1 l of distilled water and ultracentrifuged. The precipitate was treated with Nuclease P1 (manufactured by Yamasa Shoyu K.K.) and Pronase (manufactured by Calbio-chemical, U.S.A.) twice for each enzyme. Then the above-described ultracentrifugal was washed twice with distilled water and the precipitate was freeze-dried to thereby give 250 mg of a crude LPS fraction. The crude LPS fraction (250 mg) was suspended in a 50 mM Tris-HCl buffer (pH 7.4) and subjected to Sepharose 4B column chromatography (inner diameter: 1.5 cm, height: 90 cm). The excluded volume fraction was collected, precipitated from ethanol, washed with distilled water twice and then freeze-dried. Thus 110 mg of an LPS fraction was obtained. This LPS fraction was hydrolyzed with a weak acid (0.1N acetic acid) at 105° C. for 2.5 hours. Then the reaction mixture was centrifuged to give a precipitate. This fraction was purified by silica gel column chromatography (chloroform/methanol/water/triethylamine=30/12/1.5/0.1). Thus 4.5 mg of the compound of the present invention was obtained.

EXAMPLE 2: Analysis of structure

The physicochemical properties of the compound obtained in the above Example 1 were examined. The results are as follows:

(1) analysis on saccharides and fatty acids:

a. having, as the basic skeleton, a glucosamine β-(1–6) disaccharide structure, to which a phosphate group is attached to the 1-position via an ester linkage;

b. having 3-hydroxy-15-methylhexadecanoic acid attached to the amino group at the 2-position via an amide linkage;

c. having 3-hexadecanoyl-15-methylhexadecanoic acid attached to the amino group at the 2'-position via an amide linkage;

d. having no phosphate group at the 4'-position; and e. the hydroxyl groups at the 3-, 3'- and 4'-positions remaining in a free state;

(2) molecular formula:

$C_{62}H_{119}O_{17}N_2P$;

(3) color change reaction:

being positive in the sulfuric reaction, positive in the Dittmer-Lester reaction, negative in the ninhydrin reaction and negative in the TTC reaction;

(4) color and form:

a white powder;

(5) mass spectrum:

negative FAB-MS-MS, M/Z 1193 (M-H), 937 (M-2H-$C_{15}H_{31}COO$);

(6) NMR Spectrum:

$^1$H-NMR (300 MHz, $CDCl_3$+MeOD+$D_2O$) δ: 0.81 (12H, d), 0.82 (3H,t), 1.1–1.6 (72H,m, $CH_2$,CH), 2.2–2.5 (6H,m, CO-$CH_2$), 3.1–4.3 (13H,m), 4.46 (1H,d), 5.15 (1H,m), 5.45 (1H,m).

Based on these results, it was assumed that the structure of compound of the present invention is the one represented by Formula I.

EXAMPLE 3: Measurement of activity

The results of the measurement of the physiological activities of the compound of the present invention will be shown below.

(1) Mitogenic activity

The mitogenic activity was measured by, for example, determining the amount of $^3$H-thymidine incorporated into isolated and cultured mouse lymphoid cells. Namely, the spleen of a BALB/c mouse was ground and 5×10$^5$ cells/well (200 μl) of these spleen cells were incubated in the presence of the compound of the present invention at definite concentrations, in the presence of a comparative compound, or in the medium alone. Six hours before the completion of the incubation, 37 kBq/well (10 μl) of $^3$H-thymidine was added. After the completion of the incubation, the amount of $^3$H-thymidine (radioactivity) incorporated into the cells was determined. The results are expressed in "Stimulation Index" calculated in accordance with the following formula.

Stimulation Index =

$$\frac{\text{Radioactivity } (cpm) \text{ of test group}}{\text{Radioactivity } (cpm) \text{ of control group (medium alone)}}$$

As Table 1 shows, the compound of the present invention has a mitogen activity. As the comparative compound, synthetic lipid A 506 was employed. This compound 506 is 6-O-[2-deoxy-2-(3-dodecanoyloxytetradecanoylamino)-3-O-(3-tetra-decanoyloxytetradecanoyl)-4-O-phosphono-β-D-glucopyranosyl]-2-deoxy-2-(3-hydroxytetradecanoylamino)-3-O-tetradecanoyl-1-O-phosphono-α-D-glucopyranose.

TABLE 1

| Mitogen activity | | |
|---|---|---|
| Compound | | Stimulation Index |
| Invention compound | none | 1.00 |
| Invention compound | 5 μg/ml | 4.17 |
| Invention compound | 50 μg/ml | 7.46 |
| Comparative compound 506 | 50 μg/ml | 6.28 |

(2) NK (natural killer) activity

This test was carried out in the following manner. Namely, 100 μg of the compound of the present invention or the comparative compound was intravenously injected into a BALB/c mouse on the days 0 and 7. On the day 14, the spleen cells of the animal were collected. To the prepared spleen cells (1×10$^6$ cells/0.1 ml), target cells (Moloney virus-induced lymphoma YAC-1; 2×10$^4$ cells/ml) labeled with $^{51}$Cr were added followed by the incubation for 4 hours. The medium containing no spleen cell was added to the minimum free control group, while 0.1N NaOH was added to the maximum free control group. After the completion of the incubation, 0.1 ml of the culture supernatant was collected and the amount (radiation dose) of $^{51}$Cr liberated due to the damage in the target cells was measured. Then the NK activity (%) was calculated by substituting each value in accordance with the following formula.

NK Activity (%)={(Radioactivity of test group-Radioactivity of minimum free control group)(cpm)/ (Radioactivity maximum free control group-Radioactivity of minimum free control group)(cpm)}

As the result of the calculation with the use of the above formula, the compound of the present invention shows an NK activity of 50.1%. Thus it is proved to be comparable to the synthetic lipid A 506 in this activity.

(3) Antitumor activity

This test was effected by examining a cytostatic activity on methylcholanthrene-induced fibrosarcoma (Meth A). Namely, adherent cells (macrophages) were collected from spleen cells of a BALB/c mouse. To the macrophages thus prepared (2×10$^5$ cells/ml) and target cells (Meth A: 2×10$^4$ cells/0.1 ml), the compound of the present invention or the comparative compound was added to give a definite concentration. After incubating for 18 hours, 14.8 kBq/well (10 μl) of $^3$H-thymidine was added and the incubation was continued for additional 6 hours. After the completion of the incubation, the amount (radioactivity) of $^3$H-thymidine thus incorporated into the cells was measured. Then the $^3$H-thymidine-uptake suppression ratio was calculated by substituting the obtained values in accordance with the following formula and the result was expressed as the cytostatic activity on macrophages.

Cytostatic Activity (%)={1-(Radioactivity of macrophages and target cells-Radioactivity of macrophages alone)(cpm) /(Radioactivity of target cells along)}×100

The compound of the present invention showed the data as given in Table 2. Namely, it exhibited a cytostatic activity comparable to that of the synthetic lipid A 506.

TABLE 2

| Compound | | Cytostatic activity |
|---|---|---|
| Invention compound | 100 μg/ml | 64.0 |
| Invention compound | 10 μg/ml | 58.6 |

(4) Adjuvant activity

In this test, male BALB/c mice (each group having 6 animals) were used. On the days 0 and 28, 100 μg of bovine serum albumin (BSA) containing 100 μg of the compound of the present invention on the comparative compound or no such a compound was subcutaneously injected into each animal in the form of a water-in-oil type emulsion in Freund's incomplete adjuvant (FIA). On the day 5 following the booster, the level of anti-BSA IgG antibody formed in the serum was determined by the ELISA method. The result was expressed in "Stimulation Index" calculated in accordance with the following formula.

$$\text{Stimulation Index} = \frac{\text{Antibody level achieved by adding compound and } BSA \text{ to } FIA \text{ (µg/ml)}}{\text{Antibody level achieved by adding } BSA \text{ alone to } FIA \text{ (µg/ml)}}.$$

As Table 3 shows, it was found that the compound of the present invention is superior in the adjuvant activity to the synthetic lipid A 506.

TABLE 3

| Compound | Stimulation Index |
| --- | --- |
| BSA alone | 1.00 |
| Invention compound | 2.48 |
| Comparative compound 506 | 1.99 |

(5) Antiviral activity

In this test, suppression of the effect of vesicular stomatitis virus (VSV) on a mouse fibroblast line L929 was employed as an indication. Namely, $4 \times 10^4$ cells/0.1 ml of L929 cells were added to each well and incubated for 24 hours. Then 0.1 ml portions of diluted samples of the compound of the present invention or the comparative compound (1 mg/ml) from the serial dilution systems were added thereto and the incubation was continued for additional 24 hours. After discarding the culture supernatant, VSV adjusted to 100 $TCID_{50}$/0.1 ml was added and incubated for 24 hours. Then the culture medium was eliminated and fixed with a 5% solution of formaldehyde for 20 minutes. It was then stained with a 0.5% solution of Crystal Violet for 20 minutes. After washing with water and drying, the absorbance was measured at 600 nm. The activity was expressed in the reciprocal of the dilution ratio to the sample concentration (1 mg/ml) of the original sample solution wherein L929 cells survived at a ratio of 50%.

As Table 4 shows, it was found that the compound of the present invention has an antiviral activity stronger than that of the synthetic lipid A 506.

TABLE 4

| Antiviral activity | |
| --- | --- |
| Compound | Antiviral activity |
| Invention compound | 4.9 |
| Comparative compound 506 | 2.2 |

(6) Polyclonal B cell activation activity

In this test, the activity was examined by using the ELISPOT (Enzyme-Linked Immunospot) method. BALB/C mouse spleen cells ($2.5 \times 10^6$ cells) were incubated in RPMI 1640 medium containing 5% of fetal bovine serum (FBS) at 37° C. for 72 hours in the presence of a definite amount of the compound of the present invention or the comparative compound or in the absence of such a compound. After washing, the antibody-producing cells were counted by the ELISPOT method.

Namely, the above-described spleen cells were added to each well of a plate, which had been coated with goat antimouse immunoglobulin and treated with 5% FBS, and incubated for 4 hours. After washing away the cells, the plate was reacted with goat antimouse µ-chain specific antiserum labeled with biotin at 25° C. overnight, washed with physiological buffer saline (PBS) and then treated with peroxidase-labeled streptoavidin. The activity was determined by counting the spots (cells) formed by the antibody-producing cells under a stereoscopic microscope and expressed in the stimulation index, i.e., the ratio of the cell count in the presence of the test compound to the cell count in the absence of the same (control). The concentration of the test compound was expressed in µg per $2.5 \times 10^6$ cells.

As Table 5 shows, it was found out that the compound of the present invention is comparable or even superior to the synthetic lipid A 506 in the activity of activating polyclonal B cells. Thus it seemingly has a potent nonspecific protective activity.

TABLE 5

| Polyclonal B cell activation activity | | |
| --- | --- | --- |
| Compound | | Stimulation Index |
| Invention compound | none | 1.0 |
| Invention compound | 100 µg | 30.3 |
| Invention compound | 10 µg | 22.0 |
| Comparative compound | 100 µg | 20.7 |
| Comparative compound | 10 µg | 15.7 |

(7) Cytokine inducing activity

The cytokine inducing activity was tested by using an ELISA system for assaying TNF-α (manufactured by Amersham Japan) and another ELISA system for assaying IL-1β (manufactured by Otsuka Pharmaceutical Co., Ltd.). Namely, human peripheral blood monocytes ($5 \times 10^5$) were incubated in the presence of a definite concentration of the compound of the present invention or the comparative compound for 24 hours. Then the cytokines in the culture supernatant were assayed by the ELISA method.

As a result, the compound of the present invention showed little activity of inducing the production of TNF-α or IL-1β from human peripheral blood monocytes. It was also found that when the compound of the present invention (50 times as much) was added simultaneously with the synthetic lipid A 506 or LPS originating in *Escherichia coli*, the invention compound suppressed the production of IL-1β induced by the compound 506 or the LPS originating in *Escherichia coli*.

By using an ELISA system (manufactured by R & D) for assaying IL-1 receptor antagonist (IL-1ra), it was further found that the compound of the present invention produced IL-1ra in the culture supernatant of human peripheral blood monocytes in a larger amount than the synthetic lipid A 506 did.

(8) Galactosamine-loaded lethal toxicity test

The galactosamine-loaded lethal toxicity was determined by using the following experimental system.

16 mg of D-galactosamine/HCl was intraperitoneally administered to a male C57BL mouse aged 8 weeks. Immediately thereafter, the compound of the present invention was intravenously injected into the animal and the conditions were observed after 24 hours.

The compound of the present invention showed the activity as shown in Table 6 and, therefore, was proved to be less toxic.

TABLE 6

| Galactosamine-loaded lethal toxicity | |
| --- | --- |
| Compound | $LD_{50}$ |
| Invention compound | >10 µg |
| Comparative compound 506 | 0.0079 µg |

(9) Other toxicities (i) Local Shwartzman reaction

This test was carried out in the following manner. The test compound, which had been diluted to a definite concentration with 0.2 ml of physiological saline, was intradermally injected into a male rabbit. After 24 hours, 100 µg/ml/kg of *Salmonella minnesota* 9700 LPS-W (manufactured by Difco) was intravenously injected into the animal for elicitation. After 4 hours, intradermal hemorrhage was observed. As a result, the compound of the present invention caused no hemorrhage in a dose of 100 µg/site.

(ii) Pyrogenicity test

In this test, rabbits were used and 5 ml/kg of the test compound diluted to a definite concentration with physiological saline was intravenously injected into each animal. Then the rectal temperature was measured. Rabbits showing an increase in the bodily temperature by 0.6° C. or more were referred to as feverish. As a result, the synthetic lipid A 506 showed pyrogenicity in a dose of 0.01 µg, while the compound of the present invention showed no pyrogenicity even in a dose of 10 µg/kg.

(iii) Limulus test

In this test, Pregel (manufactured by Seikagaku Kogyo K.K.), i.e., a reagent for assaying an endotoxin was used. By using a freeze-dried product prepared from a *Tachypleus tridentatus* lysate, the ability to form a gel was examined. As a result, the minimum effective dose of the compound of the present invention was 1,000 times as much as that of the synthetic lipid A 506, which indicates that the invention compound has a markedly low toxicity.

That is to say, the compound of the present invention shows little toxicity in various tests including the Limulus test, the local Shwartzman reaction and the pyrogenicity test.

We claim:

1. A novel disaccharide derivative;

(1) having, as the basic skeleton, a glucosamine β-(1–6) disaccharide structure, to which a phosphate group is attached to the 1-position via an ester linkage;

(2) having 3-hydroxy-15-methylhexadecanoic acid attached to the amino group at the 2-position via an amide linkage;

(3) having 3-hexadecanoyl-15-methylhexadecanoic acid attached to the amino group at the 2'-position via an amide linkage;

(4) having no phosphate group at the 4'-position; and (5) the hydroxyl groups at the 3-, 3'- and 4'-positions remaining in a free state;

or its salt.

2. A medicinal composition comprising a compound as claimed in claim 1 or a pharmaceutically acceptable salt thereof together with pharmaceutical carriers and/or diluents.

* * * * *